_(12)_ United States Patent
Stamler (10) Patent No.: US 6,855,691 B1
(45) Date of Patent: Feb. 15, 2005

(54) METHODS FOR PRODUCING AND USING S-NITROSOHEMOGLOBINS

(75) Inventor: Jonathan S. Stamler, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 08/616,371

(22) Filed: Mar. 15, 1996

Related U.S. Application Data

(60) Provisional application No. 60/003,801, filed on Sep. 15, 1995.

(51) Int. Cl.[7] ........................ A61K 38/42; C07K 14/805
(52) U.S. Cl. .......................... 514/6; 514/2; 514/832; 530/385; 530/829; 604/28
(58) Field of Search .......................... 514/2, 6, 832; 530/385, 829; 604/28, 52

(56) References Cited

U.S. PATENT DOCUMENTS

| | | | | |
|---|---|---|---|---|
| 4,900,719 | A | | 2/1990 | Means et al. .................. 514/18 |
| 5,152,979 | A | * | 10/1992 | Hunter ..................... 424/78.38 |
| 5,380,758 | A | | 1/1995 | Stamler et al. .............. 514/562 |
| 5,395,314 | A | * | 3/1995 | Klatz et al. ................... 604/24 |
| 5,405,919 | A | | 4/1995 | Keefer et al. ................ 525/377 |
| 5,427,797 | A | | 6/1995 | Frostell et al. ............... 424/434 |
| 5,439,882 | A | * | 8/1995 | Feola et al. ..................... 514/6 |
| 5,480,866 | A | | 1/1996 | Bonaventura et al. .......... 514/6 |
| 5,574,068 | A | | 11/1996 | Stamler et al. .............. 514/562 |
| 5,593,876 | A | | 1/1997 | Stamler et al. .............. 435/188 |
| 5,863,890 | A | | 1/1999 | Stamler et al. |
| 6,087,479 | A | | 7/2000 | Stamler et al. .............. 530/363 |
| 6,255,277 | B1 | | 7/2001 | Stamler et al. |
| 6,291,424 | B1 | | 9/2001 | Stamler et al. |
| 6,583,113 | B2 | * | 6/2003 | Stamler et al. ................. 514/6 |
| 2002/0052314 | A1 | | 5/2002 | Stamler et al. |
| 2003/0007967 | A1 | | 1/2003 | Stamler et al. |
| 2003/0022267 | A1 | | 1/2003 | Stamler et al. |

FOREIGN PATENT DOCUMENTS

| | | |
|---|---|---|
| WO | WO 93/09806 | 5/1993 |
| WO | WO 93/12068 | 6/1993 |
| WO | WO 94/22306 | 10/1994 |
| WO | WO 94/22482 | 10/1994 |
| WO | WO 94/22499 | 10/1994 |
| WO | WO 95/07691 | 3/1995 |
| WO | WO 96/03139 A1 | 2/1996 |
| WO | WO 96/15797 | 5/1996 |
| WO | WO 96/16645 | 6/1996 |
| WO | WO 96/17604 | 6/1996 |
| WO | WO 96/30006 | 10/1996 |
| WO | WO 97/18000 | 5/1997 |

OTHER PUBLICATIONS

60/003,801 (currently unavailable to the Examiner).*
U.S. Appl. No. 08/123,331, filed Sep. 17, 1993, now abandoned.
U.S. Appl. No. 08/438,418, filed May 10, 1995, now U.S. 6,255,277.
U.S. Appl. No. 08/460,465, filed Jun. 2, 1995, now U.S. 6,087,479.
U.S. Appl. No. 09/433,550, filed Nov. 4, 1999, now U.S. 6,174,539.
U.S. Appl. No. 09/621,610, filed Jul. 21, 2000, now U.S. 6,471,978.
U.S. Appl. No. 09/661,190, filed Sep. 13, 2000, now U.S. 6,352,709.
U.S. Appl. No. 07/791,668, filed Nov. 14, 1991, now abandoned.
U.S. Appl. No. 07/943,835, filed Sep. 14, 1992, now abandoned.
U.S. Appl. No. 08/198,854, filed Feb. 17, 1994, now abandoned.
U.S. Appl. No. 08/287,830, filed Aug. 9, 1994, now U.S. 5,593,876.
U.S. Appl. No. 08/437,868, filed May 9, 1995, now abandoned.
U.S. Appl. No. 08/907,217, filed Aug. 6, 1997, now U.S. 5,863,890.
U.S. Appl. No. 09/092,622, filed Jun. 5, 1998, now U.S. 6,291,424.
U.S. Appl. No. 09/835,038, filed Apr. 16, 2001, published as 20020052314 (cited on PTO form 1449). The status and currently pending claims on this application are not known to Applicant.
U.S. Appl. No. 10/216,865, filed Aug. 13, 2002, published as 20030007967 (cited on PTO form 1449). The status and currently pending claims of this application are not known to Applicant.

(List continued on next page.)

*Primary Examiner*—Bennett Celsa
(74) *Attorney, Agent, or Firm*—Hamilton, Brook, Smith & Reynolds, P.C.

(57) ABSTRACT

Nitric oxide (NO) interacts with hemoglobin (Hb) at its metal centers, whereas S-nitrosothiols (RSNOs) can donate the NO group to β93 cysteine residues, thereby shielding the NO functionality from heme inactivation. S-nitrosylation of Hb is under the allosteric control of oxygen and the oxidation state of heme. NO group release from S-nitrosohemoglobin (SNO-Hb) is further facilitated by intracellular low molecular weight thiols, forming RSNOs which can be exported from the erythrocyte to regulate blood pressure. Hence, a dynamic cycle is established in which S-nitrosylation of Hb is initiated in the lung following oxygenation of red blood cells and is completed by SNO-Hb metabolism during arterial-venous transit. SNO-Hb can be formed by reaction of Hb with S-nitrosothiol. This procedure avoids oxidation of the heme. SNO-Hb in its various forms and combinations thereof (oxy, deoxy, met; S-nitrosylated to various extents) can be administered to a mammal in a method of therapy where it is desired to oxygenate, to scavenge free radicals, or to release NO groups to tissues. Thiols can also be administered to enhance the transfer of NO groups. Examples of conditions to be treated by SNO-Hb therapy include ischaemic injury, hypertension, angina, reperfusion injury and inflammations.

5 Claims, 6 Drawing Sheets

OTHER PUBLICATIONS

U.S. Appl. No. 08/281,427, filed Jul. 27, 1994, which is the priority application for WO 96/03139. Status unknown to Applicant.

U.S. Appl. No. 08/043,653, filed Apr. 6, 1993, now U.S. 5,427,797.

U.S. Appl. No. 10/066,320, filed Jan. 31, 2002, published as 20030022267 (cited on PTO form 1449). A copy of the claims currently pending is attached.

U.S. Appl. No. 10/280,085, filed Oct. 25, 2002. A copy of the claims currently pending is attached.

Search results from Derwent Work Patent Index: Stamler patent applications as of Mar. 12, 2001 (26 pages).

Stamler, Jonathan S. et al., "S–Nitrosylation of Proteins with Nitric Oxide: Synthesis and Characterization of Biologically Active Compounds," *Proc. Natl. Acad Sci. USA*, 89:444–448 (1992).

Langford, E.J. et al., "Inhibition of Platelet Activity by S–Nitrosoglutathione During Coronary Angioplasty," *The Lancet*, 344:1458–1460 (1994).

Ribeiro, JoséM.C. et al., "Reversible Binding of Nitric Oxide by a Salivary Heme Protein from a Bloodsucking Insect," *Science*, 260:539–541 (1993).

Simon, Daniel I. et al., "Effect of Nitric Oxide Synthase Inhibition on Bleeding Time in Humans," *Journal of Cardiovascular Pharmacology*, 26:339–342 (1995).

Olsen, Stephen B. et al., "Enhancement of Platelet Deposition by Cross–Linked Hemoglobin in a Rat Carotid Endarterectomy Model," *Circulation*, 93(2):327–332 (1996).

Scharfstein, Jonathan S. et al., "In Vivo Transfer of Nitric Oxide Between a Plasma Protein–Bound Reservoir and Low Molecular Weight Thiols," *J. Clin. Invest.*, 94:1432–1439 (1994).

Stamler, Jonathan S., "Redox Signaling: Nitrosylation and Related Target Interactions of Nitric Oxide," *Cell*, 78:931–936 (1994).

Arnelle, Derrick R. and Stamler, Jonathan S., "$NO^+$, $NO^{\cdot}$, and $NO^-$ Donation by S–Nitrosothiols: Implications for Regulation of Physiological Functions by S–Nitrosylation and Acceleration of Disulfide Formation," *Archives of Biochemistry and Biophysics*, 318(2):279–285 (1995).

Kondo, T. et al., "Thiol Transport from Human Red Blood Cells," *Methods in Enzymology*, 252:72–82 (1995).

Wheeler, G.P. et al., "Anti–Sickling Activity of Nitrosoureas," *Biochem. Biophys. Res. Comm.* 54(3):1024–1029 (1973).

Kosaka, H. et al., "ESR Spectral Transition by Arteriovenous Cycle in Nitric Oxide Hemoglobin of Cytokine–Treated Rats," *Am. J. Physiol.*, 266(5):1400–1405 (1994).

Kruszyna, R. et al., "Generation of Valency Hybrids and Nitrosylated Species of Hemoglobin in Mice by Nitric Oxide Vasodilators," *Toxicol. Appl. Pharmacol.*, 94(3):458–465 (1988).

Doyle, Michael P. et al., "Structural Effects in Alkyl Nitrite Oxidation of Human Hemoglobin," *Journal of Biological Chemistry*. 259(1):80–87 (1984).

Shah, N.S. et al., "Efficacy of Inhaled Nitric Oxide in a Porcine Model of Adult Respiratory Distress Syndrome," *Archives of Surgery*, 129(2):158–164 (1994).

Kukovetz, W.R. et al., "Cellular Mechanism of Action of Therapeutic Nitric Oxide Donors," *European Heart Journal*, 12 (Suppl. E):16–24 (1991).

Greenburg, A.G and Kim, H.W., "Nitrosyl Hemoglobin Formation In Vivo After Intravenous Administration of a Hemoglobin–Based Oxygen Carrier in Endotoxemic Rats," *Artif. Cells, Blood Substitutes, Immobilization Biotechnol.*, 23(3):271–276 (1995).

Clancy, Robert M. et al., "Use of Thionitrobenzoic Acid to Characterize the Stability of Nitric Oxide in Aqueous Solutions and in Porcine Aortic Endothelial Cell Suspensions," *Anal. Biochem.*, 191(1):138–143 (1990).

Charache, S. et al., "Evaluation of Extracorporeal Alkylation of Red Cells as a Potential Treatment for Sickle Cell Anemia," *Blood*, 47(3):481–488 (1976).

Feelisch, M. and Stamler, J.S., "Donors of Nitrogen Oxides," *Methods In Nitric Oxide Research*, John Wiley & Sons Ltd. (1996).

Stamler, J.S. and Feelisch, M., "Preparation and Detection of S–Nitrosothiols," *Methods in Nitric Oxide Research*, John Wiley & Sons Ltd. (1996).

Clancy, Robert M. al., "Nitric Oxide Reacts with Intracellular Glutathione and Activates the Hexose Monophosphate Shunt in Human Neutrophils: Evidence for S–Nitrosoglutathione as a Bioactive Intermediary," *Proc. Natl. Acad. Sci. USA*, 91:3680–3684 (1994).

Ignarro, Louis J. et al., "Mechanism of Vascular Smooth Muscle Relaxation by Organic Nitrates, Nitrites, Nitroprusside and Nitric Oxide: Evidence for the Involvement of S–Nitrosothiols as Active Intermediates," *The Journal of Pharmacology and Experimental Therapeutics*, 218(3):739–749 (1981).

Lancaster, Jack R., Jr., "Simulation of the Diffusion and Reaction of Endogenously Produced Nitric Oxide," *Proc. Natl. Acad. Sci. USA*, 91:8137–8141 (1994).

Butler, Anthony R. et al., "NO, Nitrosonium Ions, Nitroxide Ions, Nitrosothiols and Iron–Nitrosyls in Biology: A Chemist's Perspective," *TiPS*, 16:18–22 (1995).

\* cited by examiner

METHODS FOR PRODUCING AND USING S-NITROSOHEMOGLOBINS

RELATED APPLICATION

This application claims priority to U.S. Provisional Application No. 60/003,801 filed on Sep. 15, 1995.

GOVERNMENT SUPPORT

This invention was made with government support under Grant No. NIH RO1 HL52529 awarded by the National Institutes of Health. The government has certain rights in the invention.

BACKGROUND OF THE INVENTION

Interactions of hemoglobin (Hb) with small diffusible ligands, such as $O_2$, $CO_2$ and NO, are known to occur at its metal centers and amino termini. The $O_2/CO_2$ delivery functionalities, which arise in the lung and systemic microvasculature, are allosterically controlled. Such responsiveness to the environment is not known to apply in the case of NO. Specifically, it is thought that Hb(Fe) is involved in limiting NO's sphere of action (Lancaster, J. R., *proc. Natl. Acad. Sci. USA*, 91:8137–8141 (1994); Wood and Garthwaite, *J. Neuropharmacol.*, 33:1235–1244 (1994)), but that No does not modify the functional properties of Hb to any physiologically significant degree. Kinetic modeling based on this assumption, however, predicts that the vast majority of free NO in the vasculature should be scavenged by Hb (Lancaster 1994). Accordingly, the steady-state level of NO may fall below the Km for target enzymes such as guanylate cyclase (Lancaster 1994), if not in the unperturbed organism, then with oxidant stress such as that found in atherosclerosis. These considerations raise the fundamental question of how NO exerts its biological activity.

One answer to this paradox may be found in the propensity of nitric oxide to form S-nitrosothiols (RSNOs) (Gaston, B. et al., *Proc. Natl. Acad. Sci. USA*, 90:10957–10961 (1993)), which retain NO-like vasorelaxant activity (Stamler, J. S., et al., *Proc. Natl. Acad. Sci, USA*, 89:444–448 (1992)), but which are not subject to the diffusional constraints imposed by the high concentration of Hb in the blood. In particular, the NO group of RSNOs possesses nitrosonium ($NO^+$) character that distinguishes it from NO itself. Indeed, it is increasingly appreciated that RSNO's have the capacity to elicit certain functions that NO is incapable of (DeGroote, M. A. et al., *Proc. Natl. Acad. Sci. USA*, 92:6399–6403 (1995); Stamler, J. S., *Cell*, 78:931–936 (1994)). Moreover, consideration has been given to the possibility that —SNO groups in proteins may serve a signaling function, perhaps analagous to phosphorylation (Stamler, J. S. et al., *Proc. Natl. Acad. Sci. USA*, 89:444–448 (1992); Stamler, J. S. *Cell*, 78:931–926 (1994)). Although S-nitrosylation of proteins can regulate protein function (Stamler, J. S. et al., *Proc. Natl. Acad. Sci. USA*, 89:444–448 (1992); Stamler, J. S., *Cell*, 78:931–936 (1994)), the identification of S-nitrosoproteins within cells—the sine qua non of a regulatory posttranslational modification—has heretofore not been demonstrated.

Hemoglobin is a tetramer comprised of two alpha and two beta subunits. In human Hb, each subunit contains one heme, while the beta (β) subunits also contain highly reactive SH groups (cysβ93) (Olson, J. S., *Meth. in Enzym.*, 76:631–651 (1981); Antonini & Brunori, *In Hemoglobin and Myoglobin in Their Reactions with Ligands*, American Elsevier Publishing Co., Inc., New York, pp. 29–31 (1971)). These cysteine residues are highly conserved among species although their function has remained elusive.

NO (nitric oxide) is a biological "messenger molecule" which decreases blood pressure and inhibits platelet function, among other functions. NO freely diffuses from endothelium to vascular smooth muscle and platelet and across neuronal synapses to evoke biological responses. Under some conditions, reactions of NO with other components present in cells and in serum can generate toxic intermediates and products at local concentrations in tissues which are effective at inhibiting the growth of infectious organisms. Thus, it can be seen that a method of administering an effective concentration of NO or biologically active forms thereof would be beneficial in certain medical disorders.

SUMMARY OF THE INVENTION

The invention relates to a method of forming SNO-Hb by reaction of Hb with S-nitrosothiol in a procedure which avoids oxidation of the heme. The invention also relates to a method of therapy for a condition in which it is desired to oxygenate, to scavenge free radicals, or to release $NO^+$ groups to tissues. SNO-Hb in its various forms and combinations thereof (oxy, deoxy, met; S-nitrosylated to various extents) can be administered to a mammal in this method. Thiols can also be administered to enhance the transfer of NO groups. Examples of conditions to be treated by SNO-Hb therapy include ischaemic injury, hypertension, angina, reperfusion injury and inflammation.

DETAILED DESCRIPTION OF THE INVENTION

Roles for Hemoglobin in Physiology

The increase in SNO-Hb content of red cells across the pulmonary circuit (right ventricular inport-left ventricle) suggests that the Hb molecule is S-nitrosylated in the lung. Selective transfer of the NO group from endogenous RSNOs found in lung (Gaston, et al. (1993)) and blood (Scharfstein, et al. (1994)) to SH groups of Hb, substantiate these findings. Nonetheless, the mechanism(s) of S-nitrosylation operative in vivo is not known. The corresponding decline in Hb(FeII)NO levels across the pulmonary bed reveals a role for the lung either in the elimination of NO or in its intramolecular transfer from heme to cysβ93. Taken in aggregate, these data extend the list of function-regulating interactions of Hb with small molecules within the respiratory system, previously known to include the elimination of CO and $CO_2$ and uptake of $O_2$. Since oxygenation of Hb leads to structural changes that increase the NO-related reactivity of cysβ93, $O_2$ may be regarded as an allosteric effector of Hb S-nitrosylation. This is a newly discovered allosteric function for the protein.

The arterial-venous difference in SNO-Hb concentration suggests that the protein acts as an NO group donor in the systemic circulation. Indeed, there is good indication that SNO-Hb functions in regulation of vasomotor tone. In the microcirculation, where control of blood pressure is achieved, erythrocytes come in intimate contact with endothelial surfaces. Under these conditions, Hb can predispose the vasculature to increases in arterial resistance by sharply decreasing the steady state level of free NO (Lancaster, J. R., (1994)). This rationale is believed to contribute to the increases in blood pressure that occur with infusion of cell-free Hbs (Vogel, W. M., et al. (1986); Olsen, S. B., et al. (1996)). The transient nature of such hypertensive responses, however, would be consistent with the subsequent formation of SNO-Hb which counteracts this effect, evidenced by its lowering of blood pressure at naturally occurring concentrations. Thus, the capacity of the erythrocyte to support the synthesis and metabolism of SNO-Hb may well be important for normal blood flow.

Figure 1A:
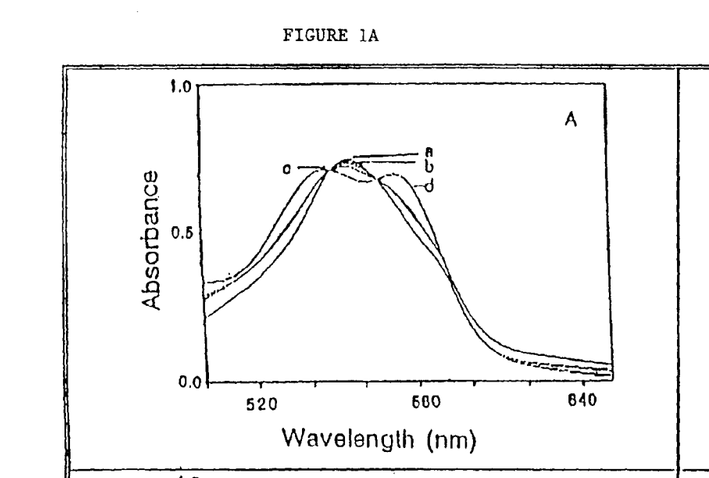
FIGS. 1A–1D are spectrographs of different forms of Hb as described in Example 1.
Figure 1B:
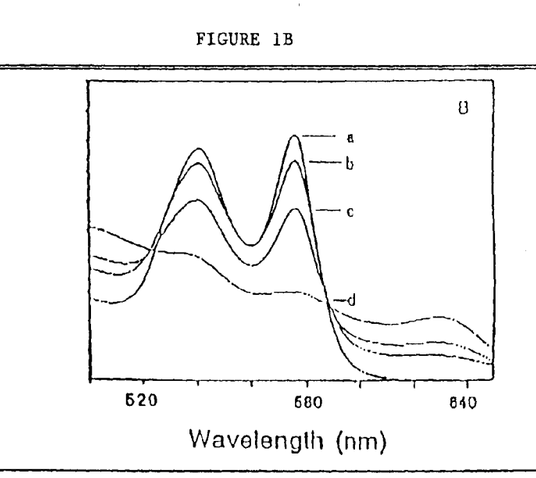
Figure 3A:
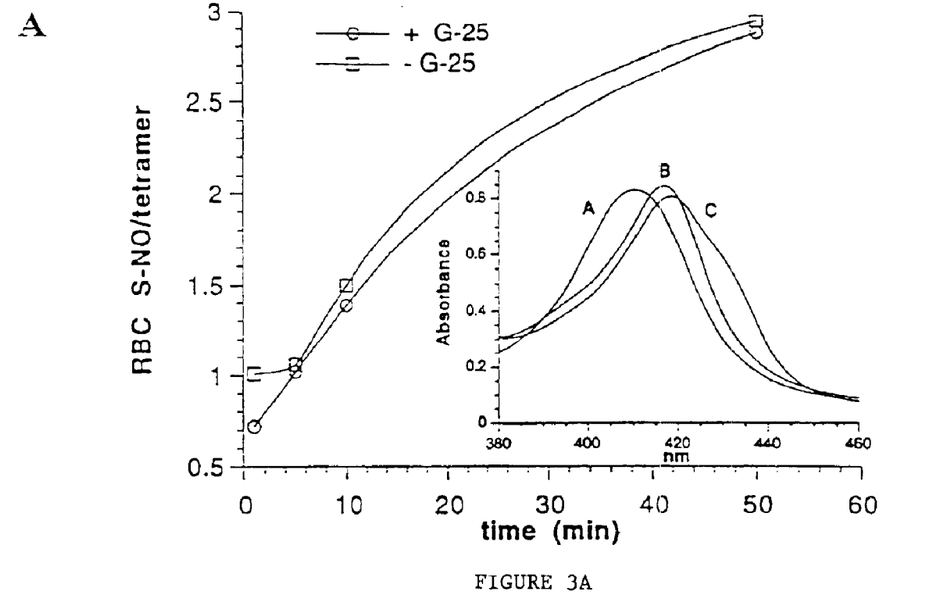
FIG. 3A is a graph showing the loading of red blood cells with S-nitrosocysteine, over time. The inset is a series of spectrographs of forms of Hb as described in Example 3.
Figure 3B:
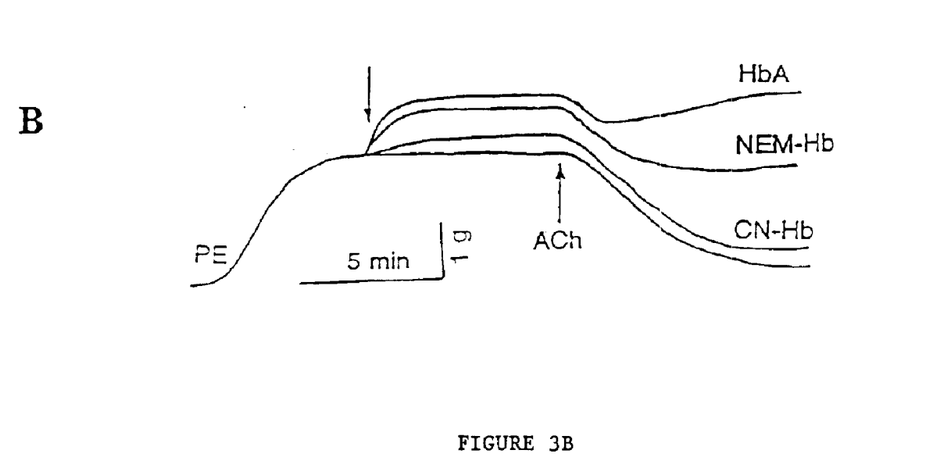
FIG. 3B is a series of tracings recording isometric tone of a rabbit aortic ring following treatment of the aortic ring with various agents as described in Example 3.
Figure 4A:
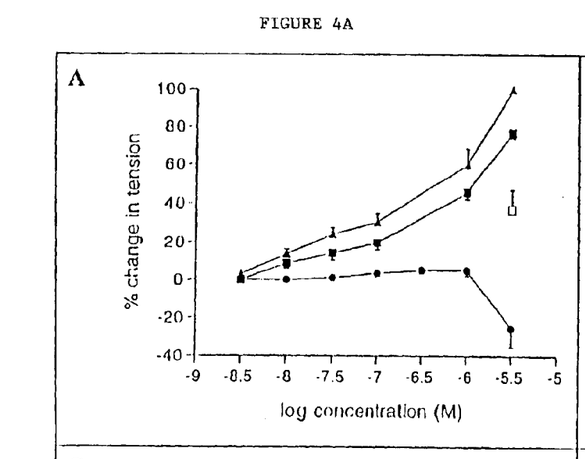
FIG. 4A is a graph of change in tension of a rabbit aortic ring versus concentration of the Hb used in the experiment.

It is implicit from this line of reasoning that mammals must have adopted unique molecular mechanisms to ensure adequate NO delivery in the microcirculation. Our results suggest that Hb may have evolved both electronic and conformational switching mechanisms to achieve NO homeostasis. Specifically, NO scavenging by the metal center(s) of SNO-Hb(FeII)$O_2$ would be sensed through its conversion to me (FeIII) (FIG. 1B). This electronic event would effect decomposition of SNO-Hb with NO group release (FIGS. 3A, 3B, 4A). In this manner, the NO-related activity of SNO-Hb would be partly determined by the amount of NO scavenged. Changes in $O_2$ tension might also function to regulate NO delivery, as we observed that NO release was facilitated by deoxygenation. It is intriguing to speculate that this allosteric effect may operate to limit the tissue $O_2$ deficit. In this scenario, NO group release would serve to regulate capillary blood flow to enhance $O_2$ delivery.

S-nitrosothiol groups in proteins have been implicated in NO metabolism and in regulation of cellular functions (Stamler, J. S., et al., *Proc. Natl. Acad. Sci USA*, 89:444–448 (1992); Stamler, J. S., *Cell*, 78:931–936 (1994)). The identification of SNO-Hb in erythrocytes is the first demonstration of an intracellular S-nitrosoprotein and gives further credence to their role in cellular regulation. The question arises as to how SNO-Hb relaxes blood vessels when any free NO released would be scavenged instantaneously by Hb itself (Lancaster, J. R., (1994)). Noteworthy in this regard are studies showing that RSNO activity involves nitrosyl ($NO^+$) transfer to thiol acceptors (Scharfstein, J. S., et al., (1994); Arnelle and Stamler, (1995); Stamler, J. S., et al., *Proc. Natl. Acad. Sci. USA*, 89:7674–7677 (1992)), which serve to protect the NO-related activity from inactivation at metal centers. Findings of this study indicate that S-nitrosothiol/thiol exchange with glutathione (forming GSNO) is likely to occur within erythrocytes, and to be influenced by the oxidation state of heme and its occupation by ligand. DeGroote and coworkers have shown that certain activities of GSNO in bacteria require transport of intact dipeptide (i.e S-nitrosocysteinylglycine) across the cell membrane (DeGroote, M. A., et al., (1995)). The data presented here expand this paradigm to include eukaryotic cells. GSNO, or related thiol carriers exported by erythrocytes (Kondo and Beutler, *Methods in Enzymology*, Packer, L., ed., Academic Press, 252:72–83 (1995)), might also initiate signaling in or at the plasmalemma (Stamler, J. S., Cell, 78:931–936 (1994)), given reports of thiol-dependent activation of potassium channels by EDRF (Bolotina, V. M., et al., *Nature,* 368:850–853 (1994)). Alternative possibilities also merit consideration. In particular, reports that Hb associates with red cell membranes via cysβ93 (Salhany and Gaines, *Trends in Biochem. Sci.*, pages 13–15 (January, 1981). This would place Hb in position to donate the NO group directly to contacting endothelial surfaces, perhaps via SNO/SH exchange. Indeed, cell surface interactions appear to be operative in signaling mediated by other S-nitrosoproteins (Stamler, J. S., et al., *Proc. Natl. Acad. Sci. USA,* 189:444–448 (1992); Stamler, J. S., *Cell,* 78:931–936 (1994)).

The highly conserved cysβ93 residues in Hb have been shown to influence the oxygenation and propensity for oxidation of the metal center, and to affect the physicochemical behavior of the protein (Garel, C., et al., (1982); Jocelyn, P. C., (1972); Craescu, C. T., et al. (1986); Mansouri, A., *Biochem. Biophys. Res. Commun.,* 89:441–447 (1979)). Nonetheless, their long sought after physiological function has remained a mystery. Our studies suggest new sensory and regulatory roles for Hb, in which cysβ93 functions in transducing NO-related signals to the vessel wall. In particular, the physiological function of cysβ93, which is invariant in all mammals and birds, is to deliver under allosteric control, NO-related biological activity that cannot be scavenged by heme. Thus, these data bring to light a dynamic circuit for the NO group in which intraerythrocytic Hb participates as both a sink and a donor, depending on the particular microenvironment of the circuit. Such observations may provide answers to paradoxes that arise from conceptual frameworks based solely on diffusional spread and reaction of free NO (Lancaster, J. R., (1994); Wood and Garthwaite, (1994)); and may have implications that extend to other thiol- and metal-containing (heme) proteins, such as nitric oxide synthase and guanylate cyclase.

Finally, the discoveries reported here may have direct therapeutic implications. Specifically, concerns over loss of NO-related activity due to inactivation by blood Hb (Lancaster, J. R., (1994)) are obviated by the presence of an RSNO subject to allosteric control. SNO-Hb is free of the adverse hypertensive properties of cell-free Hb preparations that result from NO scavenging at the metal centers. A cell-free Hb solution that mimics blood by containing SNO-Hb can be used as a blood substitute.

Further Embodiments

The subject invention relates to a method of loading cells with a nitrosating agent as exemplified for red blood cells as in FIG. 3A, but which can be accomplished in more general ways. Suitable conditions for pH and for the temperature of incubation are, for example, a range of pH 7–9, with pH 8 being preferred, and a temperature range of 25 to 37° C. For red blood cells, short incubation times of 1 to 3 minutes are preferred for limiting the formation of S-nitrosylated forms of Hb. However, intracellular concentrations of 1 mM nitrosating agent can be reached.

The nitrosating agent should be a good donor of $NO^+$ and should be able to diffuse through the cell membrane of the target cell type. That is, it must be of low molecular weight, in contrast to S-nitrosoproteins. Examples are S-nitroso-N-acetylcysteine, S-nitrosocysteinylglycine, S-nitrosocysteine, S-nitrosohomocysteine, organic nitrates and nitrites, metal nitrosyl complexes and other related nitrosating agents as defined in "Donors of Nitrogen Oxides" pp. 71–119 In *Methods in Nitric Oxide Research* (Feelisch, M. and Stamler, J. S., eds.) Wiley, Chichester, U. K. (1996), the contents of which chapter are hereby incorporated by reference in their entirety. Nitrosating agents have differential activities for different reactive groups on metal-containing proteins. A nitrosating agent can be chosen for minimal oxidation of the heme iron of Hb, and maximum activity in nitosylating thiol groups such as found on cysteine.

Such low molecular weight nitrosating agents can be used in red blood cells to deliver NO-related activity to tissues. Treatment of red blood cells with nitrosating agent further serves to increase the $O_2$ delivery capacity allows for the scavenging of oxygen free radicals throughout the circulation. Therefore, it is possible to load red blood cells with S-nitrosothiol, for example, by a process outside a patient's body after removal of whole blood (as a minimal method of isolating the red blood cells) and then to reintroduce third red blood cells into the same patient), thereby allowing the treatment of a number of types of diseases and medical disorders, such as those which are characterized by abnormal $O_2$ metabolism of tissues, oxygen-related toxicity, abnormal vascular tone, abnormal red blood cell adhesion, or abnormal $O_2$ delivery by red blood cells. Such diseases can include, but are not limited, to ischaemic injury, hypertension, shock, angina, stroke, reperfusion injury, acute lung injury, sickle cell anemia, schistosomiasis and malaria. The use of such "loaded" red blood cells also extends to blood substitute therapy and the preservation of living organs, as organs for transplantation, for example. In some cases, it may be appropriate to treat a patient with loaded red blood cells originating from a different person.

A particular illustration of the mechanism of the treatment method is presented here by considering sickle cell anemia. Sickle cell patients suffer from frequent vascular occlusive crises which manifest in clinical syndromes such as the acute chest syndrome and hepatic dysfunction. Both endothelial cell dysfunction, resulting in a clotting diathesis as well as dysfunction intrinsic to the red blood cell, are central to disease pathogenesis. At the molecular level, the increased expression of vascular adhesion molecules such as VCAM promote the adhesion of sickled red blood cells containing abnormal hemoglobin. It follows that decreasing cytokine expression on endothelial cells, promoting endothelial function and attenuating red cell sickling, are key therapeutic objectives. However, currently used therapies have been generally unsuccessful.

In this novel method for loading red blood cells with intracellular NO-donor S-nitrosothiols, the effect is to increase oxygen affinity—which in and of itself should attenuate red blood cell sickling—and to endow the red blood cell with vasodilator and antiplatelet activity, which should reverse the vasoocclusive crisis. Moreover, nitric oxide should attenuate the expression of adhesion molecules on endothelial cell surfaces, thus restoring endothelial function.

Herein is described a novel therapeutic approach to the treatment of sickle cell disease which involves loading of red blood cells with S-nitrosothiols or other nitrosating agents. Two examples of therapeutic approaches are given. In the first, the patient's own red blood cells would be S-nitrosylated extracorporeally (yielding "loaded" red blood cells) and then given to the patient. The second approach is to directly administer to a patient an agent such as S-nitrosocysteine, which is permeable to red blood cells.

For some diseases or disorders, the administration of NO-loaded red blood cells is especially desirable. Upon a change from the oxygenated to the deoxygenated state, or upon a change in the oxidation state of the heme Fe from the reduced state (FeII) to the oxidized (FeIII) state, NO is released from the thiol groups of hemoglobin, and is rapidly transferred to glutathione to form S-nitrosoglutathione. Red blood cells are known to have a high concentration of glutathione. S-nitrosoglutathione efficiently delivers NO to tissues.

In another aspect, the invention is a method for the treatment of infection by administering to an infected mammal an agent which causes S-nitrosylation of thiol groups within the cells which are the target of such agent. For example, an S-nitrosothiol to which lymphocytes are highly permeable can be administered to a patient infected with HIV. Such treatment for HIV can also be used excorporeally, to blood isolated from the patient. In another application, the infection is bacterial, and the S-nitrosothiol to be used as an anti-bacterial agent is one to which the target bacterial cells are highly permeable, as compared to the permeability properties of the host cells. (See, for example De Groote, M. A., et al., *Proc. Natl. Acad. Sci. USA* 92:6399–6403 (1995).) Alternatively, nitrosothiols can be used to treat *Plasmodium falciparum* within red blood cells.

Another embodiment of the invention is a method for specifically modifying a protein containing one or more metal atoms so that the protein becomes S-nitrosylated at one or more thiol groups without modifying the metal, as by changing the oxidation state or causing the metal atoms to bind NO. This can be accomplished by the use of a reagent which possesses $NO^+$ character, such as a nitrosothiol for instance, Example 4A), which reacts specifically with thiol groups of a protein in which metal is bound.

For hemoglobin, the nitrosation method does not affect the heme. SNO-Hb (SNO-Hb(FeII)$O_2$) can be synthesized from Hb(FeII)$O_2$ with up to 2 SNO groups per tetramer without oxidation of the heme Fe from FeII to FeIII. In contrast, when Hb(FeII)$O_2$ is incubated with excess nitric oxide or nitrite, methemoglobin (HbFe[III]) forms rapidly (Example 1B) and to a significant extent. When Hb[FeII] is incubated with nitric oxide, NO binds rapidly to the heme, forming Hb(FeII)NO to a significant extent (Example 1A).

Although rates of formation of SNO-Hb(FeII)$O_2$ from Hb(FeII)$O_2$ are more rapid (see Example 2A), the corresponding SNO-deoxyHb form can also be made by incubation of S-nitrosoglutathione or S-nitrosocysteine, for example, with Hb(FeII), yielding SNO-Hb(FeII), as in Example 1C.

The effects of the various forms of Hb on vasodilation—constriction, dilation or a neutral effect—depend on three factors: whether 1) the Fe of the heme is oxidized, 2) $O_2$ is bound at the heme (that is, the oxygenation state, dictated by the conformation of the protein as R state or T state), and 3) thiol is present in sufficient concentration to facilitate the transfer of $NO^+$.

The importance of the first factor is shown in FIG. 4A. $Hb(FeII)O_2$ and $SNO-Hb[FeII]O_2$ act as vasoconstrictors but SNO-Hb[FeIII] (met form, where FeII has been oxidized to FeIII) acts as a vasodilator. FIG. 4A shows that SNO-Hb [FeII]$O_2$ with oxygen bound at the heme, and with a ratio of SNO/Hb=2, acts as a powerful vasoconstrictor.

Figure 2A:
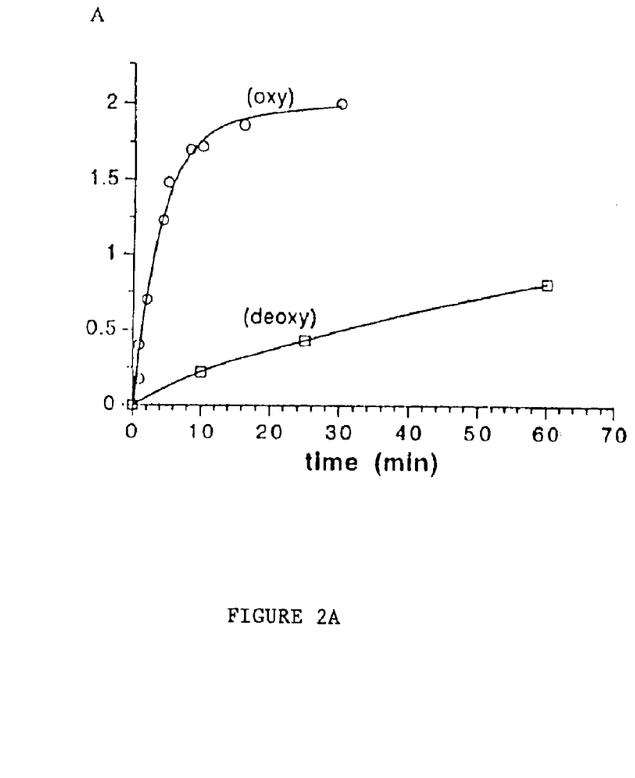
FIG. 2A is a graph showing formation, with time, of SNO-Hb by S-nitrosylation.
Figure 2B:
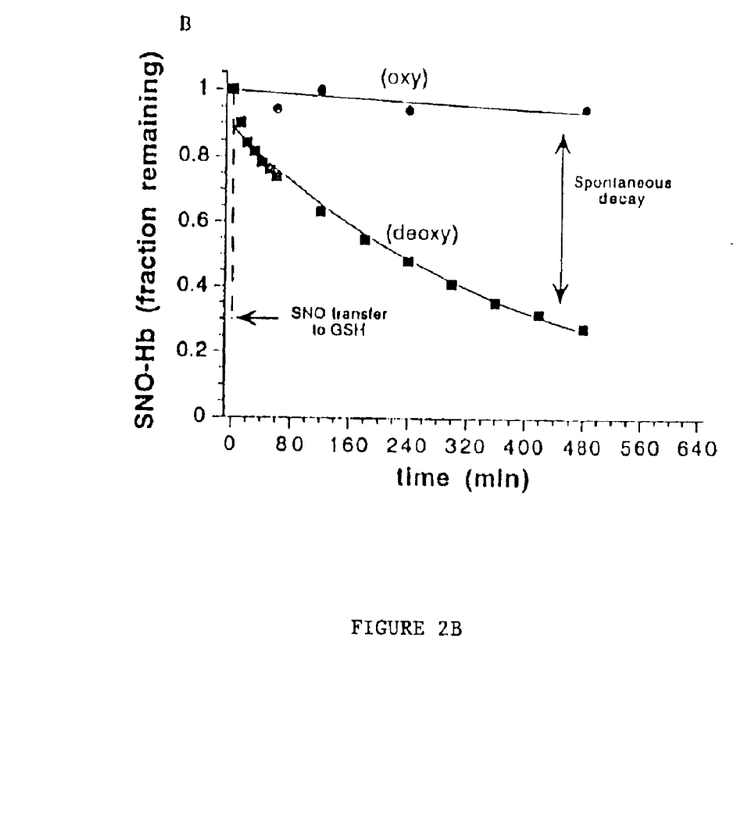
FIG. 2B is a graph showing the decomposition, with time, of oxy and deoxy forms of SNO-Hb.

SNO-Hb(FeII) is also a vasodilator. FIG. 2B illustrates the second factor in demonstrating that rates of RSNO decomposition and transfer are much faster for SNO-Hb in the deoxy state than for SNO-Hb in the oxy state.

It can be seen how the $NO^+$-donating properties of SNO-Hb depend on oxygen concentrations. SNO-Hb releases oxygen at sites of low oxygen concentration or under oxidizing conditions. SNO-Hb releases its NO group(s) to cause vasodilation either due to 1) oxidation of the heme Fe to FeIII or 2) loss of the $O_2$ from the heme by deoxygenation. It is shown in FIG. 2B that NO is transferred off SNO-Hb best in the deoxy state. In ischaemia, SNO-Hb deoxygenates, rapidly followed by the loss of NO. It can be seen from the data that SNO-metHb having a ratio of 1 SNO/SNO-metHb is a more powerful vasodilator than SNO-oxyHb having a ratio of 2 SNO/SNO-oxyHb. It should be noted that S-nitrosylation of Hb induces the R state (oxy conformation). Thus, it follows that 1 SNO-oxyHb molecule having a ratio of 1 SNO/SNO-oxyHb is less potent than 10 molecules of SNO-oxyHb having a ratio of 0.1 SNO/SNO-oxyHb.

Figure 4B:
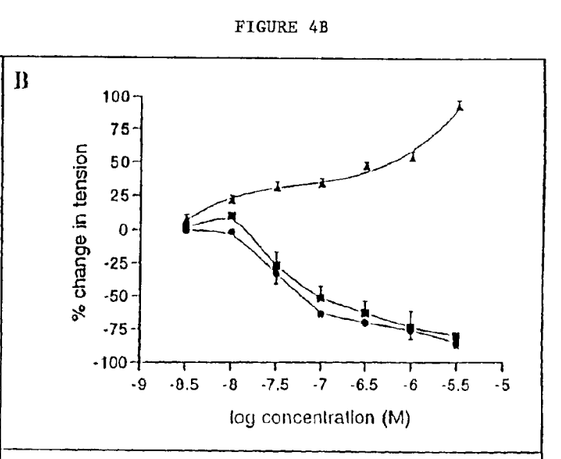
FIG. 4B is a graph of change in tension of a rabbit aortic ring versus concentration of the Hb used in the experiment, where glutathione was also added to test the effect as compared to FIG. 4A.
Figure 4C:
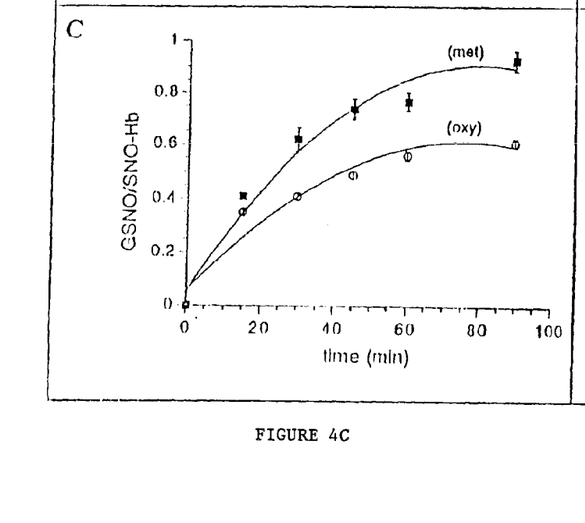
FIG. 4C is a graph of the ratio of S-nitrosoglutathione formed/starting SNO-Hb concentration versus time, showing rates of NO group transfer from oxy and met forms of Hb to glutiathione.

The third factor is illustrated by the results shown in FIG. 4B. These results demonstrate potentiation by thiol of the vasodilator effect of $SNO-Hb(FeII)O_2$ and SNO-Hb(FeIII). Transfer of $NO^+$ from SNO-Hb to low molecular weight nitrosothiols is more efficient when Hb is in the deoxy state compared to the oxy state (FIG. 2B) or in the met state compared to the oxy state (FIG. 4C).

NO is released or transferred as $NO^-$ (nitrosyl cation) from SNO-Hb. The SNO groups of SNO-Hb have $NO^+$ character. Transfer of $NO^+$ from SNO-Hb occurs most efficiently to small thiols, such as glutathione, and is most efficient when the heme is oxidized (SNO-metHb) or the SNO-Hb is in the deoxy state.

One embodiment of the invention resulting from these findings is a method of therapy that enhances the transfer of $NO^+$ from SNO-Hb to small thiols, thereby delivering NO biological activity to tissues, by the coadminstration of small molecular weight thiols, along with a form of SNO-Hb, to a mammal in need of the physiological effects of NO. To further increase the effect of NO release it is preferred that the SNO— forms of metHb or deoxyhb (or an equivalent conformation or spin state) be administered with the thiol (See FIG. 2B, for example.) A mixture of SNO-metHb and SNO-oxyHb, and possibly also thiol, can also be used. The composition and proportion of these components depends on the disease state. For example, to achieve both enhanced $O_2$ delivery and NO delivery, SNO-oxyHb can be used. Where no further delivery of $O_2$ is desirable, as in acute respiratory distress syndrome, for example, the SNO— forms of metHb and deoxyHb are especially preferred. Alternatively, the ratios of SNO/Hb can be regulated to control $O_2$ release.

Figure 5:
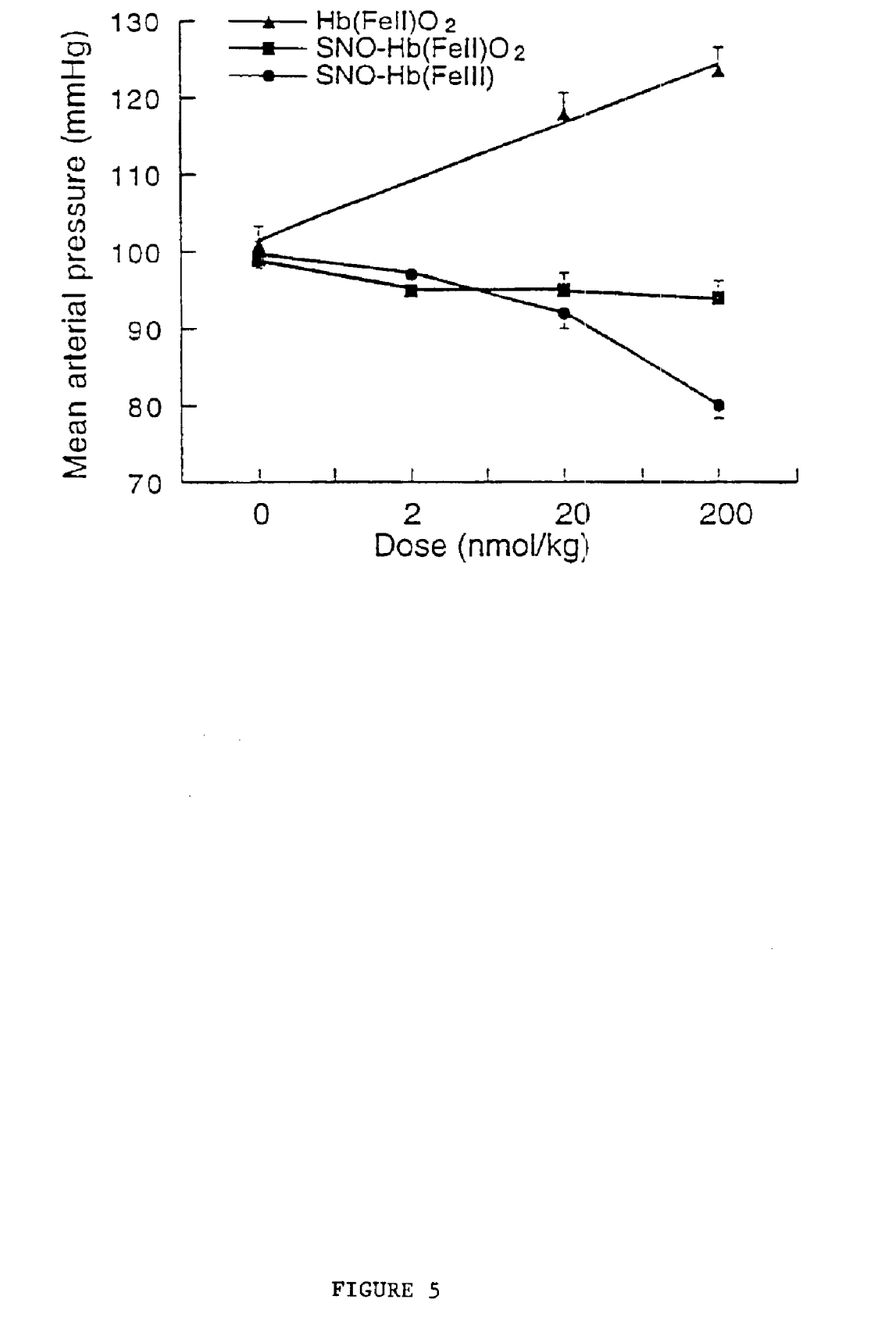
FIG. 5 is a graph showing the mean arterial blood pressure in rats after they received various doses of oxyHb (▲), SNO-oxyHb (■), or SNO-metHb (●).
Figure 6A:
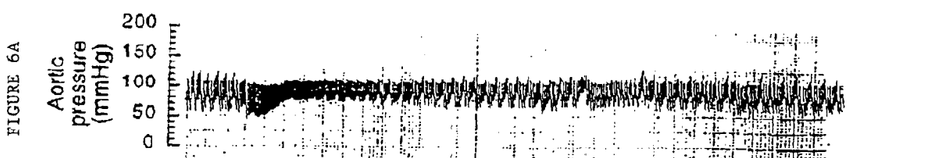
FIGS. 6A–6F are a series of tracings recording blood pressure (FIGS. 6A and 6B), coronary artery diameter (FIGS. 6C and 6D) and coronary artery flow (FIGS. 6E and 6F), after administration of S-nitrosohemoglobin to anesthetized dogs.
Figure 6B:
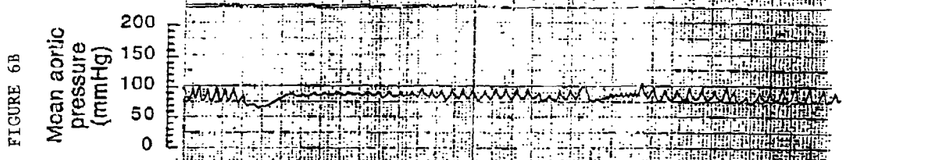
Figure 6C:
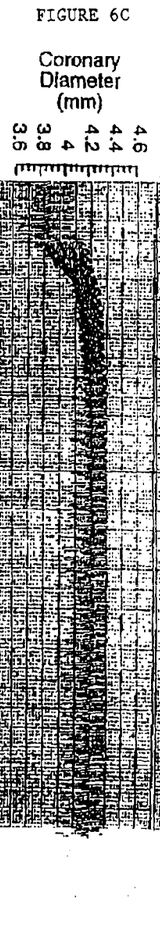
Figure 6D:
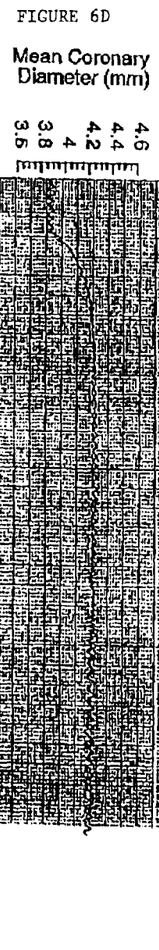
Figure 6E:
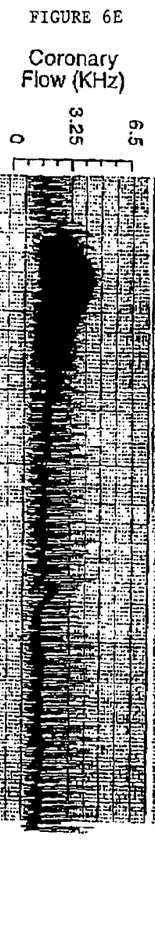
Figure 6F:
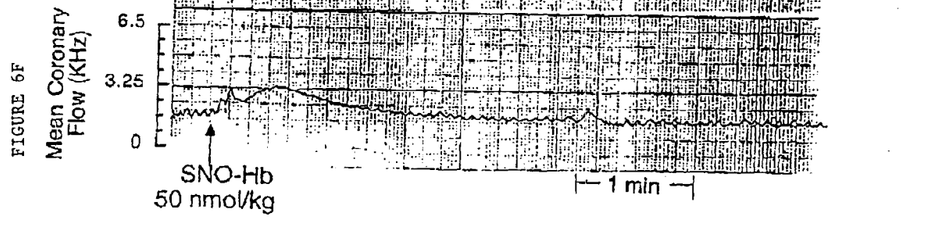

The vessel ring bioassay data of FIG. 4A agree well with the in vivo data of FIG. 5. The results of the experiments described in Example 5 confirm that $Hb(FeII)O_2$ (oxyHb) causes an increase in blood pressure in vivo, as it did also in vitro. SNO-Hb(FeIII) (SNO-metHb) causes a decrease in blood pressure in vivo as well as in vitro. $SNO-Hb(FeII)O_2$ (SNO-oxyHb) has a negligible effect on blood pressure in vivo in contrast to the increase in tension seen in the corresponding vessel ring bioassay. For SNO-oxyHb the in vivo effect is neutral. This may be explained by the constrictive effect caused by NO becoming bound to the heme being compensated by the release of NO upon deoxygenation. Therefore, SNO-oxyHb can deliver $O_2$ with minimal effect on blood pressure.

With knowledge of the results herein it is possible to synthesize Hb proteins with predicted NO-releasing properties which will constrict, late, or have no effect on blood vessels. An additional option is the choice between making oxygenated or deoxygenated forms to administer for medical conditions in which $O_2$ delivery is desirable, or undesirable, respectively.

It is possible to produce a variety of modified Hbs having specific desired properties of $O_2$ and NO delivery. For example, Hb in the R state (oxyHb) can be converted to the T state (deoxyHb) by a number of known methods. This can be done, for example, by reaction of Hb with inositol hexaphosphate. It is also known to those skilled in the art that Hb in the R state can be made, for example, by treating Hb with carboxypeptidase. Similarly, it is known that metHb can be synthesized using ferricyanide or nitrite.

Producing Hb molecules which are locked in the T state allows the synthesis of RSNO-Hb which remains in a form that is a biologically active donor of No, rather than a carrier of No. Hb which is locked in the R state can be used as a substrate for the synthesis of RSNO-Hb which carries a maximum amount of NO per molecule.

Another embodiment of the invention is a blood substitute comprising one or more forms of Hb which have been specifically S-nitrosylated to some extent at one or more thiol groups of the Hb, in order to regulate $O_2$ release and NO release. Conditions to be treated include those in which NO or $O_2$ delivery is desired, those in which NO or $O_2$ utilization is desired, or those in which No or $O_2$ is in excess. For example, in a medical condition which is characterized by the presence of an excess of oxygen free radicals and excess No, both the heme of SNO-Hb and NO released by SNO-Hb serve to trap oxygen free radicals. The heme Fe is oxidized in the process of scavenging oxygen free radicals and $NO^+$, and NO is released from the oxidized Hb by donation to a thiol, in the form of $RSNO^+$ (nontoxic). Inflammation and reperfusion injury, for example, are characterized by excess NO production and an excess of oxygen free radicals. Forms of Hb scavenge oxygen radicals and free NO, converting NO to forms that are not toxic.

A further embodiment of the invention is a method of therapy for a condition that would benefit from the delivery of No biological activity or $O_2$ or both, based on the administration of a blood substitute comprising a form of SNO-Hb. For example, SNO-Hb is useful to treat myocardial infarction. SNO-Hb has the effect of donating NO, keeping blood vessels open. SNO-Hb deoxygenates at low oxygen tension, delivering oxygen and releasing NO at the same site, thereby causing vasodilation. (See Example 7 and FIGS. 6A–6F.) These effects can be augmented by also administering thiol, either simultaneously with SNO-Hb, or before or after. For the purpose of treating myocardial infarction, for example, a high concentration or dose of SNO-Hb that has a low ratio of SNO/SNO-Hb is appropriate. Alternatively, SNO-metHb can be used for this purpose.

In another aspect, the invention is a method of enhancing NO-donor therapy by coadministering SNO-Hb together with a nitroso-vasodilator (nitroglycerin, for example) which would be otherwise consumed by the conversion of oxyHb to metHb in Hb which has not been S-nitrosylated.

The term hemoglbin or Hb as used herein includes variant forms such as mutant forms, chemically modified forms, genetically altered forms, such as fusion proteins, and truncated forms. It also includes Hbs of all species and variant forms thereof. The biological and/or chemical properties of these variant Hbs may be different from those of hemoglobins which are found naturally occurring in animals.

It will be appreciated that NO exists in biological systems not only as nitric oxide gas, but also in various redox forms and as biologically active adducts of nitric oxide such as S-nitrosothiols, which can include S-nitrosoproteins, S-nitroso-amino acids and other S-nitrosothiols (Stamler, J. S. *Cell* 78:931–936 (1994)).

A blood substitute can be a biologically compatible liquid which performs one or more functions of naturally occurring blood found in a mammal such as oxygen carrying and/or delivery, NO carrying and/or delivery, and the scavenging of free radicals. A blood substitute can also comprise one or more components of such a liquid which, when infused into a mammal, perform one or more functions of naturally occurring blood. Examples of blood substitutes include preparations of various forms of hemoglobin. Such preparations may also include other biologically active components, such as a low molecular weight thiol or nitrosothiol.

The compounds and therapeutic preparations of this invention to be used in medical treatment are intended to be used in therapeutic amounts, in suitable compositions, which can be determined by one of skill in the art. Modes of administration are those known in the art which are most suitable to the affected site or system of the medical disorder.

Suitable pharmaceutical carriers can be combined with active ingredients employed in a therapeutic preparation, if necessary. It will be appreciated that the actual amounts of the active components in a specific case will vary according to the specific component being utilized, the particular composition formulated, the mode of administration and the age, weight and condition of the patient, for example. Dosages for a particular patient can be determined by one of ordinary skill in the art using conventional considerations, (e.g. by means of an appropriate, conventional pharmacological protocol).

The present invention is more specifically illustrated in the following examples, which are not intended to be limiting in any way.

EXAMPLES

Example 1

Interactions of NO and RSNO with Hb

Figure 1C:
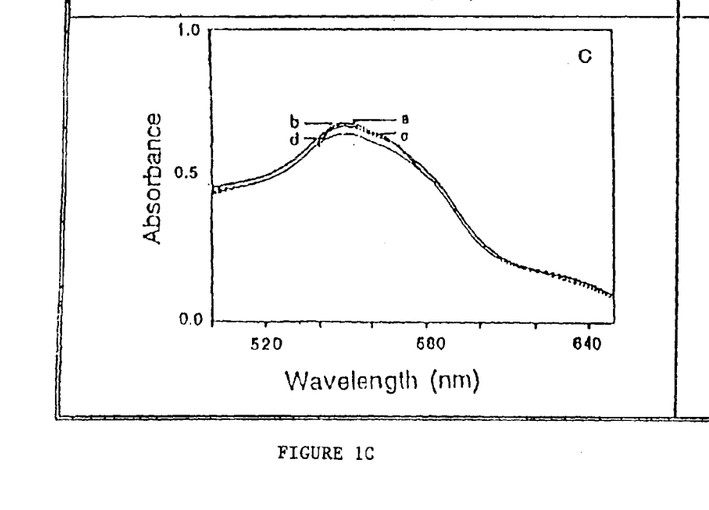
Figure 1D:
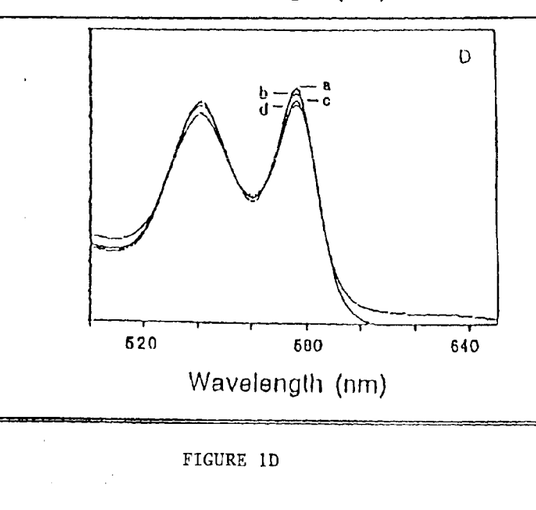

It was observed that naturally occurring N-oxides, such as NO and RSNOs (Gaston, B., et al. (1993; Scharfstein, J. S., et al., *J. Clin. Invest.*, 94:1432–1439 (1994); Clancy, R. M., et al., *Proc. Natl. Acad. Sci. USA*, 91:3680–3684 (1994)), differed markedly in their reactions with Hb. No bound very rapidly to deoxyHb (Hb[FeII]), forming relatively stable Hb[FeII]NO complexes (FIG. 1A), and converted oxyMb (Hb[FeII]O$_2$) to methemoglobin (Hb[FeIII]) and nitrate (FIG. 1B), confirming previous reports (Olson, (1981); Toothill, C., *Brit. J. Anaesthy.*, 39:405–412 (1967)). In contrast, RSNOs were found to participate in transnitrosation reactions with sulfhydryl groups of Hb, forming S-nitrosohemoglobin (SNO-Hb), and did not react with the heme centers of either deoxyHb or Hb(FeII)O$_2$ (FIGS. 1C and 1D).

A. Interaction of NO with deoxyHb

Conversion of deoxyHb (Hb[FeII]) to Hb(FeII)NO is observed upon incubation of Hb(FeII) with increasing concentrations of nitric oxide. a. Deoxy Hb. b, c, d. Reaction mixtures of NO and Hb(FeII) in ratios of 1:1, 2:1 and 10:1, respectively. The reaction product Hb(FeII)NO formed essentially instantaneously on addition of NO (i.e. within instrument dead time).

B. Interaction of NO with oxyHb

Conversion of oxyHb (Hb(Fe[II]O$_2$) to metHb (HbFe[III]) is observed upon incubation of oxyHb with increasing concentrations of NO. a. oxy Hb. b, c, d. Reaction mixtures containing NO and oxyHb in ratios of 1:1, 2:1 and 10:1, respectively. Methemoglobin formation occurred instantaneously on addition of NO (i.e. within instrument dead time).

C. Interaction of S-Nitrosothiols with deoxyHb

Conversion of Hb(FeII) to SNO-Hb(FeII) is observed upon incubation of either GSNO (shown) or S-nitrosocysteine (CYSNO) with deoxy Hb. There is little (if any) interaction of RSNO with the heme functionalities of Hb. a. deoxyHb. b, c, d. Reaction mixtures of GSNO and Hb(FeII) in ratios of 1:1, 2:1 and 10:1, respectively. Spectra were taken after 60 min of incubation in b, c, and 15 min in d. Further analysis of reaction products revealed the formation of moderate amounts of SNO-Hb in all cases. Yields of SNO-Hb (S—NO/Hb) in b, c, and d at 60 min were 2.5%, 5% and 18.5%, respectively. (See FIG. 1D and FIG. 2A.)

D. Interaction of S-Nitrosothiols with oxyHb

Conversion of Hb(FeII)O$_2$ to SNO-Hb(FeII)O$_2$ is observed upon incubation of either GSNO (shown) or CYSNO with oxyHb. There is little (if any) reaction of GSNO (or CYSNO) at the heme centers of Hb(FeII)O$_2$. Specifically, the capacity for O$_2$ binding to heme is unaffected by RSNOs. a. oxyhb. b, c, d. Reaction mixtures of GSNO and oxyHb in ratios of 1:1, 2:1, and 10:1, respectively. Spectra were taken after 60 min of incubation in the spectrophotometer. Further analysis of reaction products revealed the formation of SNO-Hb in all cases. Yields of SNO-Hb in spectra b, c and d were 5%, 10% and 50% (S—NO/Hb), respectively. In 5 other determinations, the yield of S—NO/Hb was 0.37±0.06 using GSNO (pH 7.4, 10-fold excess over Hb) and ~2 SNO/tetramer (1.97±0.06) using CYSNO (vida infra). These last data are in agreement with reports that human HbA contains 2 titratable SH groups.

Methods

Human HbA$_o$ was purified from red cells as previously described (Kilbourn, R. G., et al., *Biochem. Biophy. Res. Comm.*, 199:155–162 (1994)). Nitric oxide solutions were rigorously degassed and purified according to standard procedure (Beckman, J. S., et al., *Methods in Nitric Oxide Research*, Feelisch and Stamler, eds., Wiley Chichester, U. K. (1996)) and saturated solutions were transferred in air tight syringes. Deoxygenation of Hb was achieved by addition of excess dithionite (NO studies) or by reduction of Hb(FeII)O$_2$ through evacuation in Thunberg tubes (RSNO studies; as RSNOs react with dithionite). RSNOs were synthesized as previously described (Gaston, B., et al., (1993); Arnelle and Stamler, (1995)) Incubations with HbA$_o$ were made in phosphate buffer, pH 7.4, 0.5 mM EDTA. Quantifications of SNO-Hb were made according to the method of Saville (Gaston, B., et al., (1993); Stamler, J. S., et al., *Proc. Natl. Acad. Sci. USA*, 90:444–448 (1992)) after purification of protein with Sephadex G-25 columns. The Saville method, which assays free NO$_x$ in solution, involves a diazotization reaction with sulfanilamide and subsequent coupling with the chromophore N-(naphthyl) ethylenediamine. No low molecular weight S—NO complexes survived this purification and all activity was protein precipitable. The reactions and spectra were carried out using a Perkin Elmer UV/Vis Spectrometer, Lambda 2S.

Example 2

Allosteric Function of $O_2$ in Regulation of Hb S-Nitrosylation

Oxygenation of Hb is associated with conformational changes that increase the reactivity of cysβ93 to alkylating reagents (Garel, C., et al., *J. Biochem.*, 123:513–519 (1982); Jocelyn, P. C., *Biochemistry of the SH Group*, Academic Press, London p. 243 (1972); Craescu, C. T., et al., *J. Biol. Chem.*, 261:14710–14716 (1986)). The physiological importance of this effect was never established. We observed that rates of S-nitrosylation of Hb were markedly dependent on conformational state. In the the oxy conformation (R state), S-nitrosylation was more rapid than in the deoxy conformation (T state) (FIG. 2A). The rate of S-nitrosylation was accelerated in both conformations by alkaline conditions (i.e. rate at pH 9.2>pH 7.4), which would tend to expose the cysβ93 that is otherwise screened from reaction by the C-terminal histidine 146β. The salt bridge (asp β94—his β146) tying down the histidine residue is loosened at high pH. These data suggest that the increase in thiol reactivity associated with the R state derives, at least in part, from improved NO access rather than a conformation-induced change in pK.

A. Oxygenation Accelerates S-Nitrosylation of Hb

Rates of Hb S-nitrosylation by S-nitrosocysteine (CYSNO) are faster in the oxy conformation (Hb[FeII]$O_2$) than in the deoxy state (Hb[FeII]).

Methods

Incubations were performed using 10-fold excess CYSNO over protein (50 μM) in aerated 2% borate, 0.5 mM EDTA (oxyHb), or in a tonometer after rapid $O_2$ evacuation (deoxyHb). At shown times, samples were rapidly desalted across G-25 columns (preequilibrated with phosphate buffered saline, 0.5 mM EDTA, pH 7.4) to remove CYSNO, and analyzed for SNO-Hb by the method of Saville (Stamler, J. S., et al., *Proc. Natl. Acad. Sci. USA*, 89:444–448 (1992)).

B. Deoxygenation Accelerates Denitrosylation of Hb

Rates of RSNO decomposition (and transfer) are much faster in the deoxy conformation [SNO-Hb(FeII)] than in the oxy state [SNO-Hb(FeII)$O_2$]. The decomposition of SNO-Hb(FeII) is further accelerated by the presence of excess glutathione. Within the dead time of our measurements (~15 sec) a major fraction of SNO-Hb(FeII) was converted to GSNO.

Methods

Hbs in PBS (0.5 mM EDTA, pH 7.4) were incubated in air (oxy) or in a tonometer previously evacuated of $O_2$ (deoxy). SNO-Hb(FeII)$O_2$ decomposition was determined by the method of Saville (Saville, B., *Analyst*, 83:670–672 (1958)). Spontaneous decomposition of SNO-Hb(FeII) was followed spectrophotometrically by formation of Hb(FeII)NO. Transnitrosation reactions with glutathione were performed by addition of 100-fold excess glutathione over protein (50 μM), immediate processing of the reaction mixture under anaerobic conditions followed by rapid TCA precipitation, and analysis of RSNO in the supernatant. Rates of NO group transfer were too rapid to measure accurately by the standard methods used in this study.

Example 3

NO-related Interactions with Cysteine Residues of Hb in Physiological Systems

Given that Hb is largely contained within red blood cells, potential mechanisms by which S-nitrosylation of intracellular protein might occur were explored. Incubation of oxygenated rat red blood cells with S-nitrosocysteine resulted in very rapid formation of intracellular SNO-Hb (FeII) $O_2$ (FIG. 3A). Rapid oxidation of Hb was not observed under these conditions. Intraerythrocytic SNO-Hb also formed when red blood cells were treated with S-nitrosohomocysteine or S-nitrosocysteinylglycine, but not with S-nitrosoglutathione (GSNO). Thus, erythrocyte access of RSNOs is thiol group specific. Exposure of oxygenated red blood cells to NO resulted primarily in metHb formation.

Endothelium-Derived Relaxing Factor (EDRF) and Hemoglobin

Hb-mediated inhibition of endothelium-dependent relaxations is commonly used as a marker of NO responses. Inasmuch as reactions with either metal or thiol centers of Hb should lead to attenuated NO/EDRF (endothelium-derived relaxing factor) responses, we attempted to elucidate the molecular basis of inhibition. Hb preparations in which β93 thiol groups had been blocked with N-ethylmaleimide (NEM) or the hemes blocked by cyanmet (FeIIICN)-derivitization were studied in an aortic ring bioassay, and their activities compared with that of native Hb. Both cyanmet-Hb and NEM-Hb caused increases in vessel tone and attenuated acetylcholine (EDRF)-mediated relaxations (FIG. 3B). However, native Hb was significantly more effective than either of the modified Hb preparations (FIG. 3B). Taken in aggregate, these studies suggest that both the thiol and metal groups of Hb contribute to its. NO-related activity. To verify formation of an S-nitrosothiol in Hb, we established a bioassay in which 2 cm segments of thoracic aorta were interposed in Tygon tubing, through which 3 cc of Krebs solution containing Hb (4 μM) and; ACh (2 μM) were circulated by roller pump (1.5 cc/min×5 min). Analysis of the effluent (Gaston, B., et al., (1993)) revealed the formation of SNO-Hb (20±4 nM) in 5 of 5 experiments.

A. S-Nitrosylation of Intraerythrocytic Hb

Incubation of rat erythrocytes with S-nitrosocysteine (equimolar to heme (5 mM); phosphate buffer pH 7.4, 25° C.) leads to rapid formation of intracellular SNO-Hb(FeII) $O_2$. MetHb does not form rapidly. Separation of intracellular RSNOs across G-25 columns reveals that only a small percentage exists as low molecular weight S-nitrosothiol (e.g. GSNO) at most time points. By 60 min, 3 of the 4 available SH groups of Hb are S-nitrosylated (note that rat Hb contains 4 reactive SH groups). Inset shows spectra of SNO-Hb isolated from rat erythrocytes and related analyses. Spectrum A is that of SNO-Hb isolated from erythrocytes following G-25 chromatography. Treatment of A with dithionite results in reduction of the S—NO moiety, liberating free NO which is autocaptured by deoxy Hb, forming Hb(FeII)NO (note that dithionite simultaneously deoxygenates Hb) (spectrum C). This spectrum (C) reveals a stoichiometry of ~3 S—NOs per tetramer. The spectrum of Hb(FeII)NO containing 4 NO's per tetramer is shown for comparison (inset, spectrum B).

Methods

At shown intervals, red blood cells were pelleted rapidly by centrifugation, washed three times, lysed in deionized water at 4° C., and the cytosolic fraction subjected to rapid desalting across G-25 columns. Intracellular SNO-Hb was measured by the method of Saville (Gaston, B., et al., (1992); Stamler, J. S., et al., *Proc. Natl. Acad. Sci. USA*, 89:444–448 (1992)), and confirmed spectroscopically (inset) as described above.

B. Molecular Basis of EDRF/Hb Interaction

The effects of native Hb on EDRF responses were compared with Hb preparations in which the thiol or heme centers had been blocked by alkylation or cyanmet derivitization, respectively. All preparations of Hb elicited contractions; however, those of native Hb (in which both SH and metal centers are free for interaction) were most pronounced. Likewise, acetylcholine (ACh) mediated relaxations were most effectively inhibited by native Hb. Relaxations were inhibited to lesser degrees by cyanmet Hb (CN—Hb)(in which hemes were blocked from reaction) and NEM—Hb (in which thiol groups were alkylated by N-ethylmaleimide). These data illustrate that both heme and β93SH groups of Hb contribute to reversal of EDRF responses. Direct measurement of SNO-Hb, formed from EDRF under similar conditions, is described in the text.

Methods

Descending rabbit thoracic aorta were cut into 3 mm rings and mounted on stirrups attached to force transducers (model FT03, Grass Instruments, Quincy, Mass.) for measurement of isometric tone. The details of this bioassay system have been previously described (Stamler, J. S., et al., *Proc. Natl. Acad. Sci. USA*, 89:444–448 (1992)). Cyanmet Hb was prepared from human HbA according to published protocols (Kilbourn, R. G. et al. *Biochem. Biophy. Res. Comm.*, 199:155–162, (1994)). Alkylation of HbA with N-ethylmaleimide was followed by desalting across G-25 Sephadex to remove excess NEM. Removal of unmodified Hbcysβ93 was achieved by passage through Hg-containing affinity columns. The alkylation of free SH groups was verified using 5,5'-dithio-bis[2-nitrobenzoic acid].

TABLE 1

| ADDITIONS | % INCREASE IN TENSION (↓) | % ACh RELAXATION (↑) |
| --- | --- | --- |
| Hb (1 µM) | 40.8 ± 2.3 (n = 7) | 31.9 ± 6.9 (n = 7) |
| NEM-Hb (1 µM) | 29.4 ± 1.3 ** (n = 7) | 60.5 ± 3.9 * (n = 7) |
| CN-Hb (1 µM) | 12.9 ± 3.0 ** (n = 6) | 80.7 ± 1.0 ** † (n = 4) |
| ACh (1 µM) | | 98.3 ± 0.6 (n = 10) |

*, $P < 0.01$; **, $P < 0.001$, Compared to Hb; †, $P < 0.001$, Compared to ACh

Example 4

Transduction of SNO-Hb Vasoactivity

Arterial red blood cells contain two physiologically important forms of hemoglobin: $Hb(FeII)O_2$ and $Hb(FeIII)$ (Antonini et al. (1971)). Arterial-venous differences in the S-nitrosothiol content of intraerythrocytic Hb suggest that the NO group is released during red cell transit. Such findings raise the possibility of functional consequences, perhaps influenced by the redox state of heme and its occupation by ligand. Intriguingly, $SNO-Hb(FeII)O_2$ was found to possess modest NO-like activity when tested in a vascular ring bioassay. Specifically, the contraction elicited by $SNO-Hb(FeII)O_2$ was less than that of native $Hb(FeII)O_2$, indicating that S-nitrosylation partially reverses the contractile effects of Hb (FIG. 4A). By comparison, SNO-Hb(FeIII) was found to be a vasodilator (FIG. 4A). Notably, free NO was devoid of relaxant activity in the presence of $Hb(FeII)O_2$ or Hb(FeIII) (not shown).

Red blood cells contain millimolar concentrations of glutathione. As equilibria among RSNOs are rapidly established through RSNO/thiol exchange (Arnelle and Stamler, J. S. *Arch. Biochem. Biophy.*, 318:279–285 (1995)), the vasoactivity of SNO-Hb was reassessed in the presence of glutathione. FIG. 4B illustrates that glutathione potentiated the vasodilator activity of both $SNO-Hb(FeII)O_2$ and SNO-Hb(FeIII). GSNO formation under these conditions (confirmed chemically and in bioassay experiments) appeared to fully account for this effect. Further kinetic analyses revealed that transnitrosation involving glutathione was more strongly favored in the equilibrium with SNO-Hb (FeIII) than $SNO-Hb(FeII)O_2$ (FIG. 4C). Given the findings of steady-state levels of SNO-Hb in red blood cells (Table 2 and FIG. 3A), these results suggest that 1) the equilibrium between naturally occurring RSNOs and Hb(cysβ93) lies toward SNO-Hb under physiological conditions; 2) that transnitrosation reactions involving SNO-Hb and GSH are likely to occur within red blood cells (indeed, we have verified the presence of low molecular weight RSNOs in erythrocytes loaded with SNO-Hb); and 3) that oxidation of the metal center of Hb will shift the equilibrium toward GSNO, thereby potentially influencing bioactivity.

Additional mechanisms of NO group release from SNO-Hb were sought. Arterial-venous differences in levels of SNO-Hb raised the possibility that S—NO bond stability may be regulated by the changes in Hb conformation accompanying deoxygenation. To test this possibility, we compared the rates of NO group release from $SNO-Hb(FeII)O_2$ and SNO-Hb(FeIII). Deoxygenation was found to enhance the rate of SNO-Hb decomposition (FIG. 2B). These rates were accelerated greatly by glutathione in a reaction yielding GSNO (FIG. 2B). Our results illustrate that $O_2$-metal interactions influence S—NO affinity, and suggest a new allosteric function for Hb.

Figure 4D:
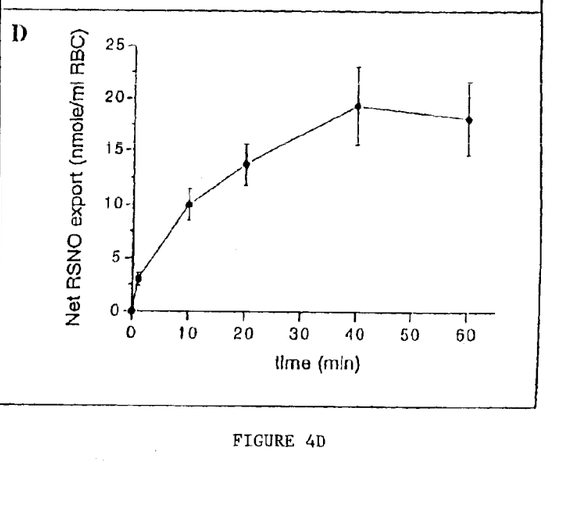
FIG. 4D is a graph of S-nitrosothiols exported from loaded red blood cells over time.

For SNO-Hb to be of physiological importance it must transduce its NO-related activity accross the erythrocyte membrane. We therefore explored this possibility by incubating erythrocytes containing SNO-Hb in physiologic buffer, and measuring the accumulation of extracellular RSNOs over time. FIG. 4D illustrates that red blood port low molecular weight (trichloroacetic acid soluble) S-nitrosothiols under these conditions. Importantly, the degree of hemolysis in these experiments was trivial (<0.5%), and correction for lysis did not significantly impact on rates of RSNO release. These results establish that an equilibrium exists between low molecular weight and protein RSNOs within the red cell, and that intracellular location is unlikely to be a limiting factor in the transduction of such NO-related activity to the vessel wall.

A. Concentration-Effect Responses of Different SNO-Hb Preparations

Contractile effects of $Hb(FeII)O_2$(▲) are shown to be partially reversed by S-nitrosylation ($SNO-Hb[FeII]O_2$(■); P=0.02 by ANOVA vs $Hb(FeIII)O_2$). Oxidation of the metal center of SNO-Hb (SNO-Hb[FeIII] (●)) converts the protein into a vasodilator (P<0.0001 by ANOVA vs SNO-Hb [FeII]$O_2$), with potency comparable to that of other S-nitrosoproteins (Stamler, J. S., et al., *Proc. Natl. Acad. Sci. USA*, 89:444–448 (1992)). The contractile properties of Hb(FeIII) are shown for comparison (□); n=6–17 for each data point.

Methods

Details of the vessel ring bioassay have been published (Stamler, J. S., et al., *Proc. Natl. Acad. Sci. USA*, 89:444–448 (1992)). $SNO-Hb(FeII)O_2$ preparations were synthesized with 10-fold excess S-nitrosocysteine (CYSNO) over $Hb(FeII)O_2$ protein (2% borate, 0.5 mM EDTA, ~15 min incubation), after which desalting was performed across Sephadex G-25 columns. CYSNO was synthesized in 0.5 N HCl, 0.5 mM EDTA and then neutralized (1:1) in 1 M phosphate buffer containing 0.5 mM EDTA. SNO-Hb(FeIII)

preparations followed a similar protocol, but used Hb(FeIII) as starting material. The latter was synthesized by treatment of Hb(FeII)O$_2$ with excess ferricyanide, followed by desalting across G-25 columns. SNO-Hb concentrations were verified spectroscopically and the S-nitrosothiol content was determined by the method of Saville (Stamler, J. S., et al., *Proc. Natl. Acad. Sci. USA*, 89:444–448 (1992)). The S—NO/tetramer stoichiometry for both SNO-Hb preparations was ~2. Oxidation of the heme was undetectable by uv-spectophotometric methods.

B. Potentiation of SNO-Hb Effects by Glutathione

Addition of glutathione (100 µM) to bioassay chambers potentiates the dose-response to both SNO-Hb(FeII)O$_2$(■) and SNO-Hb(FeIII)(●) (n=6–12; p<0.0001 for both by ANOVA, compared with the respective tracings in a). Glutathione had a transient affect on baseline tone in some experiments, and did not significantly influence the response to Hb(FeII)O$_2$ (▲).

C. Transnitrosation between SNO-Hb and Glutathione

Rates of NO group transfer from SNO-Hb (100 µM) to glutathione (10 mM) are displayed for SNO-Hb(FeII)O$_2$ (oxy) and SNO-Hb(FeIII) (met) (n=5). Data are presented as the amount of GSNO formed relative to the starting SNO-Hb concentration. The transfer is more rapid for SNO-Hb (FeIII) than SNO-Hb(FeII)O$_2$ (p<0.002 by ANOVA), suggesting that the GSNO/SNO-Hb equilibrium is shifted toward GSNO by formation of met Hb.

Methods

Thiol/SNO-Hb exchange, forming GSNO, was verified chemically (Stamler, J. S., et al., *Proc. Natl. Acad. Sci. USA*, 89:444–448 (1992)) following trichloroacetic acid precipitation (n=5). These results were verified in separate experiments by measuring the residual SNO-Hb concentration, following separation of reaction mixtures accross G-25 columns.

D. Export of S-Nitrosothiols by Red Blood Cells

Human red blood cells containing SNO-Hb are shown to export low molecular weight RSNOs over time. Hemolysis, which ranged from 0–<0.5% over one hour and did not correlate with rates of RSNO release, could account for only a trivial fraction of the measured extracellular RSNO.

Methods

Packed human red blood cells were obtained by centrifugation, washed, and resuspended in phosphate buffered saline containing 5 mM SNOCYS (0.5 mM EDTA, pH 7.4) for one hour. This results in a red cell preparation containing SNO-Hb (FeIIO$_2$/FeIII mixture) with a stoichiometry of 0.5 S—NO/tetramer. The red blood cells were then washed repeatedly to remove residual CYSNO (verified), and incubated in Krebs' solution (1:4). The accumulation of extracellular RSNO was measured over time by the method of Saville (Saville, B., *Analyst*, 83:670–672 (1958)). Hemolysis was determined by spectral analysis of red blood cell supernatants following centrifugation.

Example 5

SNO-Hb Bioactivity In Vivo

Systemic administration of cell-free Hb results in hypertensive responses which have been attributed to NO scavenging by the heme (Vogel, W. M., et al., *Am. J. Physiol.*, 251:H413–H420 (1986); Olsen, S. B., et al., *Circulation*, 93:329–332 (1996)). To determine if SNO-Hb is free of this adverse affect, and to explore if in vitro mechanisms of NO release extend to the in vivo circumstance, we compared responses to Hb and SNO-Hb infused as a bolus into the femoral vein of anesthetized rats. As illustrated in FIG. 5, Hb(FeII)O$_2$ (200 nmol/kg) caused an increase in mean arterial pressure of 20±3 mm Hg (n=4; P<0.05). In contrast, SNO-Hb(FeII)O$_2$ did not exhibit hypertensive effects and SNO-Hb(FeIII) elicited hypotensive responses (FIG. 5). Thus, the profiles of these compounds in vivo closely resemble those seen in vitro (FIG. 4A). Moreover, to demonstrate that the physiological responses of red cells are comparable to those of cell-free Hb preparations, erythrocytes containing SNO-Hb were injected into the femoral vein of rats pretreated with L-NMMA (50 mg/kg) to deplete endogenous RSNOs. At levels of SNO-Hb comparable to those found in the normal rat (0.1–0.5 µM), SNO-Hb containing red blood cells elicited hypotensive responses (8±1 mm Hg; mean±SEM; n=9), whereas native (SNO-Hb depleted) red blood cells did not (P=0.001). These changes in mean blood pressure of ~10% are on the order of those that differentiate normotension from hypertension in man, and in the therapeutic range of some antihypertensive regimens. The effects of both Hb and SNO-Hb—whether cell-free or contained within red cells—were transient, suggesting that S-nitrosylation of Hb and metabolism of SNO-Hb may be occurring in vivo, with consequent restoration of blood pressure. The bioactivity of SNO-Hb in blood, where S—NO/heme stoichiometries approach 1:50,000, is a dramatic illustration of the resistence of this NO-related activity to Hb(Fe) inactivation.

In Vivo Effects of Cell-Free Hb and SNO-Hbs

Administration of 2–200 nmol/kg Hb(FeII)O$_2$ (as a bolus) into the femoral vein of a Sprague-Dawley rat is shown to increase mean arterial pressure in a dose-dependent manner. At 200 nmol/kg, mean arterial pressure increased by 25 mm Hg (20±3 mm Hg; n=4; P<0.05). Elevations in blood pressure reversed within 10–15 min. SNO-Hb(FeII)O$_2$ infusions (over the same dose range) are shown to ameliorate Hb(FeII) O$_2$-induced hypertension without causing overt changes in blood pressure. A similar response was seen at higher doses. By comparison, SNO-Hb(FeIII) infusions caused a significant fall in mean arterial pressure (pre 108±4 mm Hg; post 74±6 mm Hg, n=5; P<0.05) at the highest dose (200 nmol/kg). Hypotensive responses tended to be transient with blood pressure normalizing over 10 minutes. A fall in blood pressure was also seen with injection of erythrocytes containing SNO-Hb.

Methods

Rats were anesthetized by intraperitoneal injection of pentobarbital and the femoral arteries and veins accessed by local cut down. The artery was then cannulated and the blood pressure monitored continuously using a Viggo Spectramed pressure transducer attached to a Gould recorder. An IBM PC (DATA Q Codas) was used for data acquisition.

Example 6

Loading of Red Blood Cells With S-Nitrosothiols

Incubation of rat erythrocytes with S-nitrosocysteine (equimolar to heme (5 mM); phosphate buffer pH 7.4, 25° C.) leads to rapid formation of intracellular S-nitrosothiols. MetHb does not form rapidly. Separation of cell content across G-25 columns establishes the formation of intraerythrocytic low molecular weight S-nitrosothiol e.g. S-nitrosoglutathione, (GSNO). By 2 min., one can achieve as much as millimolar GSNO.

Method for assay of RSNO

S-nitrosocysteine (5 mM) treated red blood cells are pelleted rapidly by centrifugation, washed three times, lysed in deionized water at 4° C., and the cytosolic fraction subjected to rapid desalting across G-25 columns. Intracellular RSNO is measured by the method of Saville and can be confirmed spectroscopically.

Effects on Blood Pressure from Loaded Red Blood Cells

Red blood cells treated with S-nitroscysteine (to produce SNO-RBCs) and introduced into the femoral vein of a Sprague-Dawley ray decreased mean arterial pressure in a dose-dependent manner. For red blood cells in which SNO-Hb was assayed at 0.3 $\mu$M (the endogenous in vivo SNO-Hb concentration), arterial pressure decreased by 8±1 mm Hg (mean±SEM for 9 experiments; p<0.001 compared to untreated red blood cell controls). For red blood cells in which SNO-Hb was assayed at 0.5 $\mu$M, arterial pressure decreased by 10 mm Hg. For red blood cells in which SNO-Hb was assayed at 0.1 $\mu$M (a sub-endogenous SNO-Hb concentration), arterial pressure decreased by 6 mm Hg. The administration of untreated red blood cells caused no effect or a slight increase in arterial blood pressure. Administration of L-monomethyl-L-arginine (L-NMMA; 50 mg/kg) caused an increase in blood pressure of about 20 mm Hg. Changes in blood pressure from a bolus administration of offloaded red blood cells lasted 15–20 minutes.

Further Methods

Rats were anesthetized by intraperitoneal injection of pentobarbital and the femoral arteries and veins accessed by local cut down. The artery was then cannulated and the blood pressure monitored continuously using a Viggo Spectramed pressure transducer attached to a Gould recorder. An IBM PC (DATA Q Codas) was used for data acquisition.

Example 7

Effects of SNO-Hb on Coronary Vasodilation, Coronary Flow and Blood Pressure

SNO-Hb was synthesized as described in Example 4A. Completion of the reaction was determined as described in Example 4A. Twenty-four healthy mongrel dogs (25–30 kg) were anesthetized with intravenous thiamylal sodium (60–80 mg/kg) and subjected to left thoracotomy in the fourth intercostal space. The left circumflex coronary artery distal to the left atrial appendage was minimally dissected. A pair of 7-MHz piezoelectric crystals (1.5×2.5 mm, 15–20 mg) was attached to a Dacron backing and sutured to the adventitia on opposite surfaces of the dissected vessel segment with 6-0 prolene. Oscilloscope monitoring and on-line sonomicrometry (sonomicrometer 120-2, Triton Technology, San Diego, Calif.) were used to ensure proper crystal position. A pulse Doppler flow probe (10 MHz, cuff type) was implanted distal to the crystals. An inflatable balloon occluder was also placed distal to the flow probe. All branches of the circumflex artery between the crystals and the occluder were ligated. Heparin sodium-filled polyvinyl catheters were inserted into the left ventricular cavity via the apex, into the left atrium via the atrial appendage, and into the ascending aorta via the left internal thoracic artery. The catheters, tubing, and wires were tunnelled to a subcutaneous pouch at the base of the neck.

After a 10 to 15 day recovery period, the catheters and wires were exteriorized under general anesthesia, and 2–3 days later, each dog was given a bolus injection of SNO-Hb (0.4 mg) to evaluate vascular response. Two dogs that demonstrated <5% dilation of epicardial coronary vessels were excluded from subsequent studies, and two were excluded because of other technical reasons.

Dogs were trained and studied while loosely restrained and lying awake in the lateral recumbent position. The laboratory was kept dimly illuminated and quiet. Aortic pressure, left ventricular end-diastolic pressure dP/dt external coronary diameter and coronary flow were monitored continuously. In 10 dogs, 0.1 ml of SNO-Hb solution, 50 nM/kg, was injected via the left atrial catheter. To verify potential effects of solvent on vasculature, 0.1 ml injections of 30% ethanol in distilled water were given as vehicle control. Between injections, phasic coronary blood flow and coronary artery diameter were allowed to return to preinjection levels (minimum 15 minutes). Allowing a 15 minute period between injections resulted in no modification of repeated dose injections. To assess the direct and potential flow mediated indirect vasodilation effects of SNO-Hb on the conductance vessels, the dose was repeated in 6 of 10 dogs with partial inflation of the adjustable occluder to maintain coronary blood flow at or slightly below preinjection levels. The response to acetylcholine chloride (Sigma Chemical) was assessed in another group of 10 dogs following a similar protocol to that used for SNO-Hb.

Epicardial coronary diameter, coronary blood flow, heart rate, and aortic and left ventricular end-diagnostic pressures were compared before and after each SNO-Hb injection. The maximum changes in coronary dimension and blood flow were expressed as a function of increasing doses of SNO-Hb. The response of coronary dimension to increasing doses followed a characteristic sigmoid dose-response curve that could be described by the following equation:

$$\text{Effect} = \frac{\text{maximal effect} \times \text{dose}}{K_D + \text{dose}}$$

where $K_D$ is the drug-receptor complex dissociation constant and is the dose at which 50% of the maximum response ($EC_{50}$) is achieved. In each animal, a nonlinear least-squares regression ($r^2 > 0.90$) was performed on the dose-response data. The regression was constrained to the above equation. From the regression, values for maximum response and $K_D$ were obtained for each individual animal. The mean of these values was then calculated to obtain an average $K_D$ and maximum response for the study group. These values were used to generate a mean curve, which was plotted with the mean dose-response values. (See FIGS. 6A–6F.)

Example 8

Endogenous Levels of S-Nitrosohemoglobin and Nitrosyl(FeII)-Hemoglobin in Blood

To determine if SNO-Hb is naturally occuring in the blood, and if so, its relationship to the $O_2$ transport capacity and nitrosylated-heme content of red cells, we developed an analytical approach to assay the S-nitrosothiol and nitrosyl-heme content of erythrocytes (Table 2). Arterial blood was obtained from the left ventricle of anesthetized rats by direct puncture and venous blood was obtained from the jugular vein and inferior vena cava. Hb was then purified from red cells and assayed for RSNO and (FeII)NO content. Arterial blood contained significant levels of SNO-Hb, whereas levels were virtually undetectable in venous blood (Table 2). Measurements made 45 minutes after infusion of the NO synthase inhibitor $N^\omega$-monomethyl-L-arginine (L-NMMA) (50 mg/kg), showed a depletion of SNO-Hb as well as total Hb-NO (82, and 50±18%, respectively; n=3–5; p<0.05). These data establish the endogenous origin of SNO-Hb, although some environmental contribution is not excluded. The arterial-venous distribution seen for SNO-Hb was reversed in the case of Hb(FeII)NO, which was detected in higher concentrations in partially deoxygenated (venous) erythrocytes (Table 2). Accordingly, the proportion of nitrosylated protein thiol and heme appears to depend on the oxygenation state of the blood. Consistent with these findings, Wennmalm and coworkers have shown that Hb(FeII)NO forms mainly in venous (partially deoxygenated) blood (Wennmalm, A., et al., *Br. J. Pharmacol.*, 106(3):507–508 (1992)). However, levels of Hb(FeII)NO in vivo are typically too low to be detected (by EPR) and SNO-Hb is EPR-silent (i.e. it is not paramagnetic). Thus, photolysis-chemiluminesence represents an important technological advance, as it is the first methodology capable of making quantitative and functional assessments of NO binding to Hb under normal physiological conditions.

Methods

Blood was obtained from the left ventricle (arterial) and jugular vein (venous) of anesthetized Sprague-Dawley rats. Comparable venous values were obtained in blood from the inferior vena cava. Red blood cells were isolated by centrifugation at 800 g, washed three times in phosphate buffered saline at 4° C., lysed by the addition of 4-fold excess volume of deionized water containing 0.5 mM EDTA, and desalted rapidly across G-25 columns according to the method of Penefsky at 4° C. In 24 rats, Hb samples were divided in two aliquots which were then treated or not treated with 10-fold excess $HgCl_2$ over protein concentration as measured by the method of Bradford. Determinations of SNO-Hb and Hb(FeII)NO were made by photolysis-chemiluminescence as described below. In 12 additional rats, further verification of the presence of SNO-Hb was made by assaying for nitrite after $HgCl_2$ treatment. Specifically, samples (with and without $HgCl_2$) were separated across Amicon-3 (Centricon filters, m.w. cut off: 3,000) at 4° C. for 1 h, and the low molecular weight fractions collected in airtight syringes containing 1 $\mu$M glutathione in 0.5 N HCl. Under these conditions, any nitrite present was converted to S-nitrosoglutathione, which was then measured by photolysis-chemiluminescence (detection limit ~1 nM). SNO-Hb was present in all arterial samples, and levels determined by this method (286±33 nM) were virtually identical to and not statistically different from those shown in Table 2. In venous blood, SNO-Hb was undetectable (0.00±25 nM); levels were not statistically different from those given above.

Method for Assay of S-Nitrosohemoglobin

A highly sensitive photolysis-chemiluminescence methodology was employed. A somewhat similar assay has been used for measuring RSNOs (S-nitrosothiols) in biological systems (Gaston, B., et al., (1993); Stamler, J. S., et al., (1992)). The method involves photolytic liberation of NO from the thiol, which is then detected in a chemiluminesence spectrometer by reaction with ozone. The same principle of operation can be used to cleave (and measure) NO from nitrosyl-metal compounds (Antonini, E. Brunori, M. In *Hemoglobin and Myoglobin in Their Reactions with Ligands*, American Elsevier Publishing Co., Inc., New York, pp. 29–31 (1971)). With adjustment of flow rates in the photolysis cell, complete photolysis of the NO ligand of Hb(FeII)NO could be achieved. Standard curves derived from synthetic preparations of SNO-Hb, Hb(FeII)NO, and S-nitrosoglutathione were linear (R>0.99), virtually superimposable, and revealing of sensitivity limits of approximately 1 nM. Two analytical criteria were then found to reliably distinguish SNO-Hb from Hb(FeII)NO: 1) signals from SNO-Hb were eliminated by pretreatment of samples with 10-fold excess $HgCl_2$, while Hb(FeII)NO was resistant to mercury challenge; and 2) treatment of SNO-Hb with $HgCl_2$ produced nitrite (by standard Griess reactions) in quantitative yields, whereas similar treatment of Hb(FeII)NO did not. UV/VIS spectroscopy confirmed that NO remained attached to heme in the presence of excess $HgCl_2$.

TABLE 2

Endogenous levels of S-nitrosohemoglobin and nitrosyl(FeII) - hemoglobin in blood

| Site | SNO-Hb (nM) | Hb(FeII)NO (nM) |
| --- | --- | --- |
| Arterial | 311 ± 55* | 536 ± 99 † |
| Venous | 32 ± 14 | 894 ± 126 |

\* $P < 0.05$ vs venous; † $P < 0.05$ for paired samples vs venous

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method for preserving a living organ, comprising incubating the organ in a solution of S-nitrosated hemoglobin and low molecular weight thiol.

2. A method for enhancing the preservation of an excised organ, comprising storing the organ in a solution comprising an effective amount of SNO-Hb(FeII)$O_2$.

3. A method for treating a human with sickle cell anemia comprising administering to the human an effective amount of a preparation comprising SNO-Hb(FeII)$O_2$.

4. The method of claim 3 in which the preparation comprises SNO-Hb(FeII)$O_2$ and a thiol.

5. The method of claim 3 in which the preparation comprises SNO-Hb(FeII)$O_2$ and an S-nitrosothiol.

* * * * *